United States Patent [19]

Mann et al.

[11] Patent Number: 5,387,707

[45] Date of Patent: Feb. 7, 1995

[54] NEW ROUTE OF SYNTHESIS FOR TERTIARY ALKYL ESTERS

[76] Inventors: John Mann, University of Reading, Department of Chemistry The University, Whiteknights, Reading RG6 2AD; Caroline J. Springer, Cancer Research Campaign Laboratories, Dept., of: Medical Oncology, Charing Cross Hospital, Fulham Palace Road, London W6 8RF, both of United Kingdom

[21] Appl. No.: 838,281

[22] PCT Filed: Sep. 5, 1990

[86] PCT No.: PCT/GB90/01371

§ 371 Date: Apr. 10, 1992

§ 102(e) Date: Apr. 10, 1992

[87] PCT Pub. No.: WO91/03460

PCT Pub. Date: Mar. 21, 1991

[30] Foreign Application Priority Data

Sep. 5, 1989 [GB] United Kingdom ................ 8920011

[51] Int. Cl.[6] .................... C07C 303/00; C07C 309/15
[52] U.S. Cl. ............................ 558/48; 560/16; 564/162
[58] Field of Search ............................ 558/48

[56] References Cited

FOREIGN PATENT DOCUMENTS

88/07378 10/1988 WIPO .

OTHER PUBLICATIONS

"Novel Prodrugs Which Are Activated to Cytotoxic Alkylating Agents by Carboxypeptidave G1" Springer et al., *J. Med.* (1990) 33(2):677–681.

*Primary Examiner*—José G. Dees
*Assistant Examiner*—Dwayne C. Jones
*Attorney, Agent, or Firm*—Morrison & Foerster

[57] ABSTRACT

4-[(2-chloroethyl)-(2-hydroxyethyl)-amino]benzoyl amino acids of formula (IV), wherein X represents a group (a), where Pro represents hydrogen or a straight or branched chain $C_{1-6}$ alkyl group, and salts thereof, and processes for their production. The compounds are useful for the production of nitrogen mustard prodrugs

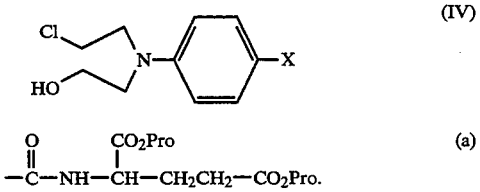

4 Claims, No Drawings

NEW ROUTE OF SYNTHESIS FOR TERTIARY ALKYL ESTERS

FIELD OF THE INVENTION

This invention relates to pro-drugs and is particularly concerned with novel intermediates for production of enzyme activatable pro-drugs.

DESCRIPTION OF THE RELATED ART

Over the years, many cytotoxic compounds have been discovered which are of potential use in cancer chemotherapy. Nitrogen mustards form one important family of such cytotoxic compounds. The clinical use of cytotoxic compounds in general and nitrogen mustards in particular has been limited because of the poor selectivity in the cytotoxic effect between tumour cells and normal cells.

One approach to overcome this problem has involved the development of so-called pro-drugs which are derivatives of the cytotoxic drug, often a relatively simple derivative, whose cytotoxic properties are considerably reduced compared to those of the Parent drug. Numerous proposals have been made for the administration of such pro-drugs to patients under regimes whereby the pro-drug is only converted to the cytotoxic drug in the region of the intended site of action.

One particularly promising approach involves the conversion of the nitrogen mustard into a reaction product with an amino acid or oligopeptide to for a pro-drug which can be converted to the parent nitrogen mustard at the site of intended action under the influence of an enzyme. This approach can be put into practice by the utilization of an antibody/enzyme conjugate in association with a pro-drug. The antibody/enzyme conjugate is one formed from an antibody to tumour associated antigen and an enzyme that will convert the pro-drug to the cytotoxic drug. In clinical practice, the antibody/enzyme conjugate is first administered to the patient and is allowed to localize in the region of the tumour to be treated. The pro-drug is then administered to the patient so that conversion of the pro-drug to the cytotoxic drug is also localized in the region of the tumour to be treated under the influence of the localized enzyme. Such a system is described in International Application PCT/GB88/00181, published as WO88/07378.

Specific pro-drugs that can be used in the above-mentioned International Application are those based upon benzoic acid nitrogen mustards. The cytotoxic benzoic acid nitrogen mustard is converted, in accordance with the procedures described in our above-mentioned International Application, into an amide by reaction with an alpha-amino acid, the preferred alpha-amino acid being glutamic acid. In this case, the glutamic acid is linked to the nitrogen mustard through an amide bond formed between the carboxy group of the benzoic acid nitrogen mustard and the alpha-amino group of the glutamic acid.

Other pro-drugs can be prepared based on benzoic acid nitrogen mustards where the carboxy group is converted into a derivative with an oligopeptide or other protecting group which is removed in vivo, under the influence of an enzyme localized in the region of the tumour to be treated.

Pro-drugs of the type described in the above-mentioned Application and other pro-drugs embodying the same principle are administered as pro-drugs where the carboxy groups present in the glutamic acid or analogous residue, for example aspartic acid, are in free carboxylic acid form. These pro-drugs are prepared by synthetic methods in which the carboxy group present in the glutamic acid or analogous reactant is protected.

One pro-drug of particular interest is the compound of the formula (I):

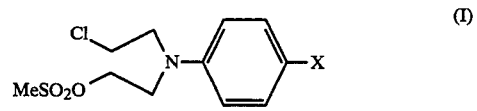

wherein X represents a group

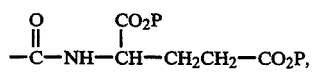

and where P is a protecting group or hydrogen. The protecting group may be a straight or branched chained $C_{1-6}$ alkyl, for example ethyl or tertiary butyl. The compound of the formula (I) can be prepared from a compound of formula (II):

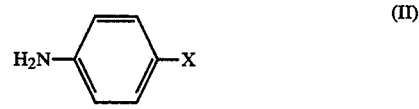

The above mentioned International Application describes the synthesis of compound (I) from compound (II) via an intermediate (III):

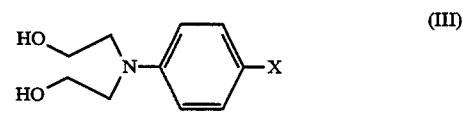

by reaction of (III) with methanesulphonyl chloride in pyridine. However, this reaction results in three major products, since the hydrogens of the two terminal hydroxy groups may each be substituted by a mesyl group and the resulting bis mesyloxy groups may in turn be substituted by a chloro group. The three products have to be separated by column chromatography before removal of the protecting groups. Column chromatography is not suitable for large scale preparation of compounds and is therefore a restriction on the quantity of the compound (I) which may be prepared on a commercially viable scale.

SUMMARY OF THE INVENTION

It has now been found that the compound of formula (I) may be synthesized in high yield from a novel intermediate of formula (IV):

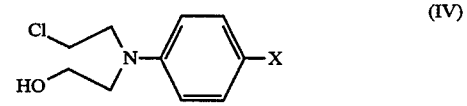

where X is as defined in formula (I) by reaction of (IV) with methane sulphonyl chloride in an organic solvent, for example triethylamine. Since IV is produced as a single main product, it may be purified by recrystallization.

Accordingly, the present invention provides 4-[(2-chloroethyl)(2-hydroxyethyl)-amino]benzoyl amino acids (CHA) for use in the production of 4-[(2-chloroethyl)(2-mesyloxyethyl)amino]benzoyl amino acids (CMA).

A further embodiment of the invention provides a process for the production of CMA by reaction of CHA with methane sulphonyl chloride.

References to CMA and CHA, and precursors thereof, in the above and following text, are to be understood to include compounds in which the terminal carboxy groups of the amino acid moiety are protected by a group P as defined above. References to these compounds (CHA, CMA and precursors thereof) also include salts thereof. Preferably, these will be pharmaceutically acceptable salts. Such salts include alkali metal (e.g. sodium), alkaline earth metal (e.g. magnesium) and ammonium salts, and acid addition salts such as the hydrochloride salt.

The compound of formula IV may be synthesized from the novel intermediate (V):

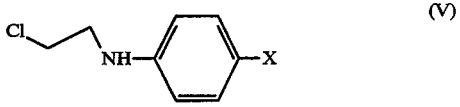

(V)

Where X is as defined in formula I above by reaction of (V) with ethylene oxide in glacial acetic acid.

The compound of formula (V) may be synthesized by the reaction of compound (II) with chloroacetaldehyde in the presence of a borohydride, such as a cyanoborohydride, e.g. a metal salt of cyanoborohydride such as sodium cyanoborohydride or in the presence of a transition metal catalyst, e.g. palladium or platinum, and hydrogen.

The compound of formula II may be made either by reference to the above mentioned International Application or by reference to the Example given below.

Thus in accordance with the present invention there is also provided:

i) a process for the production of 4-[(2-chloroethyl)amino]benzoyl amino acids (CA) by the reaction of 4-aminobenzoyl amino acid with chloroacetaldehyde and cyanoborohydride;
ii) CA suitable for use in the production of CHA;
iii) a process for the production of CHA by reaction of CA with ethylene oxide;
iv) a process for the production of CMA which comprises reacting CA with ethylene oxide to produce CHA, and reacting the resulting CHA with methane sulphonyl chloride to obtain CMA;
v) a process for the production of CMA which comprises reacting 4-aminobenzoyl amino acids with chloroacetaldehyde to produce CA followed by the process described in (iv) above;
vi) a process for the production of CMA which comprises reacting 4-nitrobenzoyl amino acids with ammonium formate in the presence of a palladium catalyst on charcoal to produce the corresponding 4-aminobenzoyl amino acid, followed by the process described in (v) above, and;
vii) the process described in paragraphs (iv), (v) or (vi) above in which the amino acid moieties of the CA, 4-aminobenzoyl amino acids or 4-nitrobenzoyl amino acids are protected by a group P (as defined above), preferably a tertiary butyl ester group, and the resulting CMA is deprotected by treatment with trifluoroacetric acid or formic acid.

During the synthesis of the compound of formula (I) the one or more carboxylic acid groups of the amino acid moiety will be protected. The protecting groups such as ethyl ester groups may be removed by alkaline hydrolysis with sodium hydroxide, as described in the above mentioned International Application, or where the protecting groups are tertiary butyl ester groups by treatment with trifluoroacetric acid in a substantially non-aqueous medium, or with formic acid. After removal of the protecting groups, the de-protected pro-drug may be recovered by lyophilization (freeze drying) and stored in the dried state. When necessary, the de-protected pro-drug may be transferred into vials and frozen, for example in liquid nitrogen, before freeze-drying. On industrial freeze-dryers, pre-freezing is however not usually necessary. Lyophilization may be performed by standard techniques known in the art.

The invention is further illustrated by the following specific reaction scheme and examples:

REACTION SCHEME FOR EXAMPLES 1 AND 2

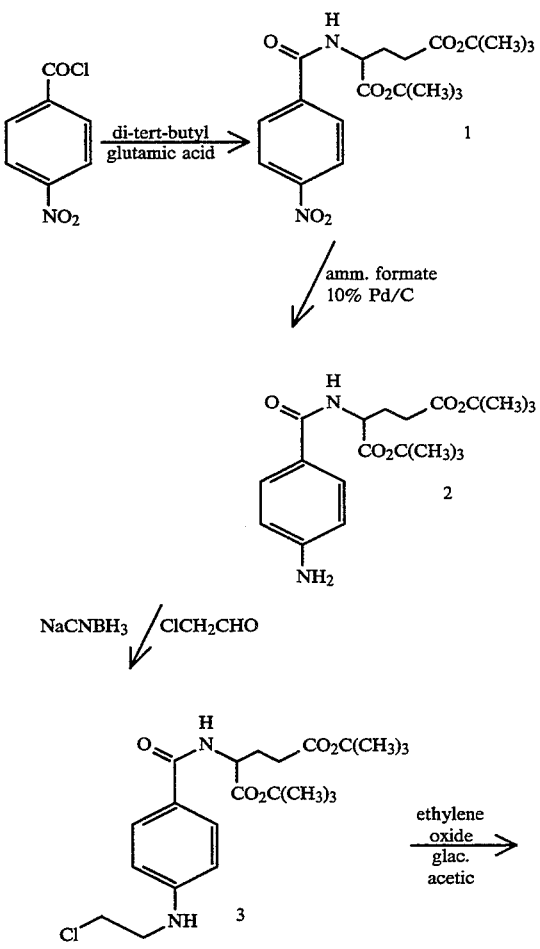

-continued
REACTION SCHEME FOR EXAMPLES 1 AND 2

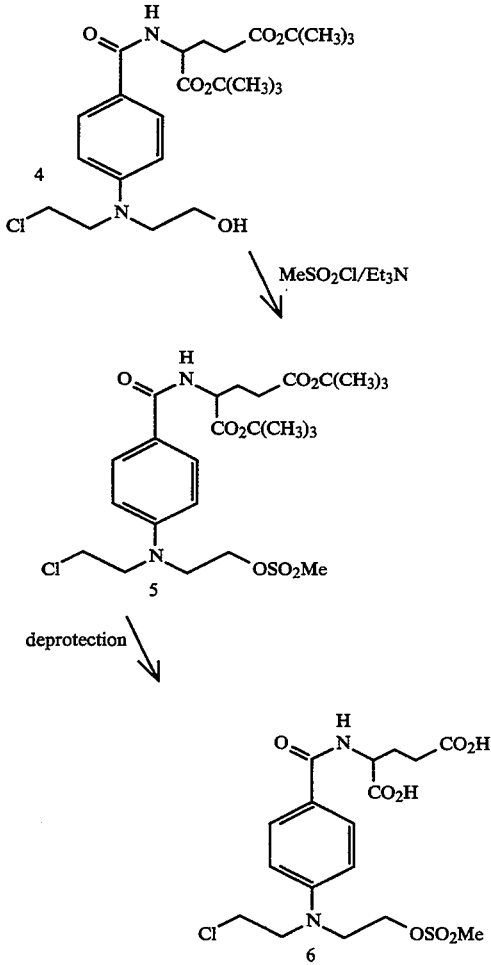

EXAMPLE 1

Synthesis of the Glutamic Acid di-t-butylester 10 g (68 mmol) glutamic acid in 290 ml t-butylacetate and 16.6 ml (0.15 mol) of 60% perchloric acid were shaken for about 15 min until the amino acid and the perchloric acid were dissolved. The solution was kept at room temperature for 5 d.

The mixture was cooled to −5° C. (ice/NaCl) and extracted with 0.5N hydrochloric acid (4×). The aqueous phase was neutralized with solid sodium carbonate and extracted with ether (6×). The combined organic phases were washed with saturated aqueous sodium bicarbonate (2×), dried over magnesium sulphate and evaporated to give 3.5 g (20%) of the glutamic acid di-t-butylester as a pale yellow liquid.

1. Synthesis of Compound 2

1.1 Synthesis of Compound 1

3.5 ml (25 mmol) of triethylamine was added to a cooled (ice/NaCl) solution of 5.3 g (20 mmol) glutamicacid-d-t-butylester in 70 ml dry dichloromethane. At that temperature 3.7 g (20 mmol) p-nitrobenzoylchloride in 60 ml dry dichloromethane were added dropwise and the solution was stirred overnight at room temperature.

The solution was washed with water (5×), dried over magnesium sulphate and evaporated to form an orange oil.

$^1$H-NMR (CDCl$_3$ 60 MHz): δ=1.43 (s, 3CH$_3$), 1.5 (s, 3CH$_3$), 1.87–2.6 (m, 4H, CH$_2$), 4.4–4.83 (m, 1H, N—C—H), 7.2–7.63 (d, broad, 1H, N—H), 7.8–8.33 (m, 4H, arom. H) ppm.

1.2 Synthesis of Compound 2

1.1 g of 10% palladium on charcoal and 6.6 g (0.105 mol) ammoniumformate were added to the cooled (ice-water) solution of the crude compound 1 in 60 ml dry methanol (exothermic reaction).

The reaction mixture was stirred at room temperature for ½ h.

During that time the product precipitated. Dichloromethane was added to dissolve the precipitate and the catalyst was removed by filtration through a celite pad. The filtrate was evaporated and the residue was taken up in water and dichloromethane. The phases were separated. The organic phase was washed with water, dried over magnesium sulphate and evaporated to give 2 as colorless precipitate.

Yield 6.55 g (87%) of 2, mp. 130° C. (after recrystallization from ethanol/petrolether (40°-60° C.).

$^1$H-NMR (CDCl$_3$60 MHZ): δ=1.41 (s, 3CH$_3$), 1.48 (s, 3CH$_3$), 2.0–2.6 (m, 4H, CH$_2$), 3.8–4.13 (s, broad, 2H exchangeable, NH$_2$), 4.47–4.9 (m, 1H, N—C—H), 6.4–6.87 (m, 3H, 1N—H 2 arom. H) 7.6 (d, J=8 Hz, 2H, arom. H) ppm.

2. Synthesis of Compound 4

2.1 Synthesis of the Diester 3

1.5 ml of a 1:1 mixture of 6N aqueous hydrochloric acid and methanol, 1.5 ml (10 mmol) chloroacetaldehyde as a 45% aqueous solution and 0.554 g (9 mmol) sodium cyanoborohydride were added successively to a solution of 3.05 g (8 mmol) dipeptide 2 in 60 ml dry methanol.

The reaction mixture was stirred at room temperature for 5 d, then acidified with some concentrated hydrochloric acid to pH 1–2 and evaporated. The residue was taken up in dichloromethane and water. The organic layer was separated and the aqueous layer was extracted with dichloromethane. The combined organic layers were washed with water (2×) and 10% aqueous sodiumbicarbonate solution (1×), dried over magnesium sulphate and evaporated to give the crude 3. Another batch was purified by flash chromatography (R$_F$=0.44, SiO$_2$, ether/petrolether 2:1) on silica gel with ether/petrolether (40°-60° C.) (2:1) as eluant and recrystallization with a little dichloromethane, ether and petrolether (40°-60° C.) to afford 3 as colorless crystals (mp. 144.5°-144.7° C.).

IR (CHCl$_3$): 3356 (broad, N—H), 3010 (C—H), 1712 (C=O), 1610, 1500, 1437, 1148 cm$^{-1}$.

$^1$H-NMR (CDCl$_3$ 220 MHz): δ=1.43 (s, 9H, CH$_3$), 1.50 (s, 9H, CH$_3$), 1.95–2.54 (m, 4H, CH$_2$), 3.54 (t, J=5.3 Hz, 2H, CH$_2$), 3.7 (t, J−5.3 Hz, 2H, CH$_2$), 4.5–4.82 (m, 2H, 1N—H, exchangeable, 1 N—C—H), 6.6 (d, J=8.8 Hz, 2H, arom. H), 6.85 (d, J=8.4 Hz, 1H, O=C—N—H), 7.68 (d, J=8.8 Hz, 2H, arom.H) ppm.

$^{13}$C-NMR (CDCl$_3$): δ=27.72 (1CH$_2$), 28.03 (6CH$_3$), 31.70 (1CH$_2$), 42.93 (1CH$_2$ ), 44.87 (1CH$_2$ ), 52.62 (1N—C—H) , 80.65 (1O—C—), 82.17 (1O—C—), 111.96 (2 arom. C—H), 122.70 (1 arom. C—C=O), 128.90 (2 arom. C—H), 150.10 (1 arom. C—N), 166.73 (1C=O), 171.62 (1O—C=O), 172.5 (1O—C=O) ppm.
Ms: m/e=440 (M+), 182 (100%).

microanalysis: found C 59.98%, H 7.67%, N 6.30%, calculated for $C_{22}H_{33}ClN_2O_5$ C 59.92%, H 7.54%, N 6.35%.

2.2 Synthesis of Dipeptide 4

Gaseous ethylene oxide was passed through a solution of the crude 3 in 50 ml glacial acetic acid at room temperature for ¾ h. The solution was stirred in a stoppered flask at room temperature for 2 d.

The solution was diluted with 60 ml of water and extracted with dichloromethane (3×). The combined organic phases were washed with water, dried over magnesium sulphate and evaporated in vacuo. The residue was purified by flash chromatography on silica gel with ether as eluant ($R_F$=0.22, $SiO_2$ ether) to afford 2.537 g (65%) 4 as colorless precipitate.

759 mg 4 were recrystallized from a little dichloromethane, ether and petrolether (40°-60° C.) to give 483 mg 4 as colorless crystals (mp. 97°-99° C.).

IR ($CHCl_3$): 3429 (broad, NH, OH), 3009 (C—H), 1719 (C=O), 1607, 1498, 1437, 1150 $cm^{-1}$.

$^1$H-NMR ($CDCl_3$ 220 MHz): δ=1.42 (s, 9H, $CH_3$), 1.49 (s, 9H, $CH_3$), 1.92-2.52 (m, 4H, $CH_2$), 2.65 (s, broad, 1H, exchangeable, OH), 3.54-3.72 (m, 4H, $CH_2$), 3.72-3.86 (m, 4H, $CH_2$), 4.60-4.80 (m, 1H, N—C—H), 6.68 (d, 2H, J=8.8 Hz, arom.H), 6.88 (d, 1H, J=8.4 Hz, N—H), 7.68 (d, 2H, J=8.8 Hz, arom.H) ppm.

MS: m/e=484 (M+), 448 (M+-HCl), 190 (100%)

microanalysis: found C 59.32%, H 7.71%, N 5.65%, calculated for $C_{24}H_{37}ClN_2O_6$ C 59.43%, H 7.69%, N 5.78%.

3. Synthesis of Compound 5

1.5 ml of triethylamine and 0.5 ml (6.5 mmol) methanesulfonylchloride were added to 2.605 g (5.67 mmol) 4 in 50 ml dichloromethane at 5° C. After stirring 1 h at 5° C. the reaction mixture was poured into 300 ml of water. The phases were separated and the aqueous phase extracted with dichloromethane (2×). The combined organic phases were washed with water (3×), dried over magnesium sulphate and evaporated. The crude product 5 was crystallized from ether/petrolether (40°-60° C.) to give 2.336 g (75%) as colorless crystals (mp. 74.5°-75.5° C.).

IR ($CHCl_3$): 3430 (N—H), 3009 (C—H), 1722 (C=O), 1648, 1608, 1496, 1368 ($SO_2$—O), 1175, 1153 $cm^{-1}$.

$^1$H-NMR ($CDCl_3$. 220 MHz): δ=1.44 (S, 9H, $CH_3$), 1.51 (s, 9H, $CH_3$), 1.94-2.52 (m, 4H, $CH_2$), 2.95 (s, 3H, $CH_3$), 3.68 (t, J=6.2 Hz, 2H, $CH_2$), 3.76-3.9 (m, 4H, $CH_2$), 4.39 (t, J—5.5 Hz, 2H, $CH_2$), 4.63-4.74 (m, 1H, N—C—H), 6.71 (d, J=8.8 Hz, 2H, arom. H), 6.82 (d, J=7.5 Hz, 1H, N—H), 7.76 (d, J=8.8 Hz, 2H, atom. H) ppm.

EXAMPLE 2

The di-t-butyl ester 5 (3.00 g, 5.33 mmol) produced in Example 1 is stirred in formic acid (98%, 600 ml) at 10° C. for 48 h. It is then transferred into vials and frozen in liquid nitrogen, prior to lyophilization on a freeze dryer. When all the acid has been removed, the vials are capped while still under vacuum on the freeze dryer. The deprotection is quantitative and gives the dicarboxylate 6 as a white powder as final product (2.40 g, 100%)

NMR. ($Me_2SO$—$d_6$) δ1.98 (m,2H, $CH_2CH_2CO_2H$), 2.34 (t,2H, J=7.3 Hz, $CH_2CH_2CO_2H$), 3.16 (s,3H, $CH_3SO_3$), 3.77 (s, 4H, $ClCH_2CH_2$), 3.83 (t, 2H, J=5.4 Hz, $CH_3SO_3CH_2CH_2$), 4.33 (m, 3H, $CH_3SO_3CH_2CH_2$ & CH), 6.82 (ABq, 2H, J=8.9 Hz, arom H—3,5), 7.77 (ABq, 2H, arom H—2,6), 8.27 (d, 1H, J=7.8 Hz, NH) mass spectrum FAB m/z 451 ([M+H+], 17%), 401 (M—$ClCH_2$, 7%), 304 (M—$NHCH(CO_2H)CH_2CH_2CO_2H$, 100%)

Anal. $C_{17}H_{23}N_2O_8ClS\cdot 0.2H_2O$)

| Expected | Found |
|---|---|
| C 44.92 | 44.89 |
| H 5.19 | 5.41 |
| N 6.17 | 5.78 |
| Cl 7.79 | 7.83 |
| 7.05 | 6.97 |

EXAMPLE 3

The di-t-butyl ester 5 (92 g, 163 mmol) produced in Example 1 is stirred in formic acid (98%, 18.4 l) at 10° C. for 48 hours. It is then transferred into vials and placed in a LSL-secfroid FCFV600 freeze dryer (Life Sciences Labs)

The solution is frozen in situ prior to lyophilisation when all the acid has been removed, the vials are capped while still under vacuum on the freeze dryer. The dicarboxylate 6 is obtained as a white powder (68 g, 92%).

Anal. $C_{17}H_{23}N_2O_8ClS$

| Expected | Found |
|---|---|
| C 45.28 | 45.09 |
| H 5.14 | 5.41 |
| N 6.21 | 6.41 |
| Cl 7.86 | 7.76 |
| S 7.11 | 7.40 |

We claim:

1. A process for the preparation of a compound of the formula (I)

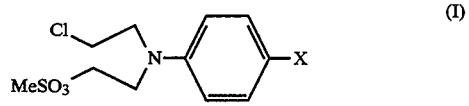

or a salt thereof wherein X represents a group

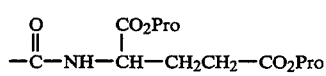

where Pro represent hydrogen or a straight or branched Chain $C_{1-6}$ alkyl group, which comprises reacting a compound of formula (IV)

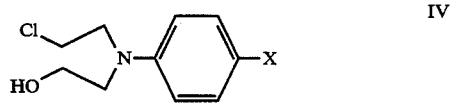

or a salt thereof, where X is as defined above, with methane sulfonyl chloride in an organic solvent.

2. A process according to claim 1 wherein in the moiety X, the groups Pro are both ethyl.

3. A process according to claim 1 wherein in the moiety X, the groups Pro are both t-butyl.

4. A process according to claim 3 which further includes removal from the moiety X of both t-butyl groups by deprotection in the presence of formic acid.

* * * * *